United States Patent [19]

Daniel

[11] Patent Number: 4,644,595

[45] Date of Patent: Feb. 24, 1984

[54] PORTABLE MOTORIZED BED LIFT APPARATUS

[76] Inventor: R. A. Daniel, 9859 N. 110th Ave., Sun City, Ariz. 85351

[21] Appl. No.: 792,679

[22] Filed: Oct. 29, 1985

[51] Int. Cl.[4] .................................................. A61F 5/00

[52] U.S. Cl. ............................................ 5/81 R; 5/87; 128/69; 128/75

[58] Field of Search ...................... 5/81 R, 81 B, 81 C, 5/83, 84, 85, 86, 87, 88, 89; 128/69, 75

[56] References Cited

U.S. PATENT DOCUMENTS

| | | | |
|---|---|---|---|
| 773,803 | 7/1903 | Black | 5/86 |
| 2,565,536 | 8/1951 | Valentine | 5/87 X |
| 2,666,212 | 1/1954 | Flanders | 5/87 |
| 3,275,296 | 9/1966 | Meyer | 5/81 R |
| 3,659,594 | 5/1972 | Schwab | 5/87 X |

FOREIGN PATENT DOCUMENTS

| | | | |
|---|---|---|---|
| 591172 | 1/1934 | Fed. Rep. of Germany | 5/86 |

*Primary Examiner*—Carl D. Friedman
*Assistant Examiner*—R. Chilcot
*Attorney, Agent, or Firm*—Charles P. Padgett, Jr.

[57] ABSTRACT

A portable motorized bed lift apparatus is provided for enabling a prone patient who is disabled, handicapped, an invalid, or the like to raise himself to a sitting position with the weight of his upper body portion substantially over his hips without the benefit of outside human assistance. The lifting apparatus of the present invention includes a derrick-like assembly and a motor driven cable and pulley arrangement for operating the derrick-like structure. The derrick-like structure includes a pair of elongated runner-like leg members adapted to be positioned at least partially under a patient's bed from the foot toward the head. A base support interconnects the rear end of the leg members and vertically mounts a substantially elongated mast. A pair of angle supports further connects the leg members to the mast for support purposes. A boom member is pivotably mounted to the mast at its mid-portion and extends forwardly in the direction of the leg members out over the body of the prone patient and suspends a handlebar mechanism from the forward end which is adapted to be gripped by the patient for lifting purposes.

20 Claims, 6 Drawing Figures

PORTABLE MOTORIZED BED LIFT APPARATUS

BACKGROUND OF THE INVENTION

1. Field of the Invention

The present invention relates generally to a derrick-like bed lift apparatus, and more particularly to a portable motorized bed lift for enabling a disabled or invalid person who is normally prone on a bed to achieve a sitting position with his upper body over his hips without human assistance so that a patient can leave the bed for one purpose or another.

2. Description of the Prior Art

There are many people who spend most, if not all, of each day of their lives lying in a prone position on a bed. These people often feel totally helpless since they must call upon others for help in rising, going to the bathroom, getting into and out of wheelchairs and the like. It is critical, both from a physical and a psychological standpoint, that these people not be made to feel helpless. It is very important that they be able to do simple things for themselves such as, for example, rising to a sitting position from a prone position without the outside intervention of another human being.

Many of these people have severe disabilities such as the loss of hip bones, severe deterioration of muscles, and the like. Most such patients can maintain a balance once they are in a sitting position by locking the joints of their legs and or arms. From this position, the patient can get out of bed and slide into a wheelchair or the like to go to the bathroom, to their favorite TV seat, into an automobile, and the like.

In order to aid such patients in attaining a sitting position, the proper type of lift is a generally horizontal pull and vertical lift of the shoulders and upper torso to a position which substantially distributes the person's upper body weight over the persons hips. The prior art has recognized this problem but has failed to achieve any type of solution. While various bed lifts are known in the art, they usually involve some type of seat apparatus which the severely disabled person simply cannot get into without outside human assistance.

For example, U.S. Pat. No. 4,387,473 which issued on June 14, 1983 to Donald F. Gettner for a PATIENT HANDLER discloses a chair-type lift apparatus which can be placed in either a sitting or a prone position. It has support assemblies for use in maintaining the patient handler in a given position so that it can be moved to different locations when being used by a patient. However, in all such instances, a severely disabled or injured person cannot get himself into the patient handler without the assistance of one or more third parties. Actually, the patient handler is designed for use in moving the patient about after he is placed in the chair or prone handler position, and not to enable the patient to do anything by himself.

Similarly, U.S. Pat. No. 3,999,228 issued on Dec. 28, 1976 to Dale H. Thomas for an INVALID LIFTING AND WALKING DEVICE. This patent teaches a derrick-like assembly which is motorized by electric batteries and which is used to enable an invalid to lift himself to a standing position and walk about by propelling the apparatus with him. The hoist is not designed for lifting a prone person out of the bed but only for aiding a standing person to walk about. It is designed so that the patient, by himself, cannot even reach the controls when in the prone position, and again, third party assistance is required for manipulating the patients body to a standing position and arranging the harness or straps about him so that he can walk about.

Still further, patents such as U.S. Pat. No. 1,450,950 which issued on Apr. 10, 1923 and U.S. Pat. No. 1,641,388 which issued on Sept. 2, 1927, both to S. S. Jenkins for an INVALID LIFTER AND CARRYING APPARATUS cannot be used by a patient without outside assistance. One teaches a chair-type apparatus while the other teaches a bed-type apparatus, and in both, the patient must be initially placed on the lift or carrier by third parties and cannot assume this position on his own.

Lastly, U.S. Pat. No. 4,484,366 issued on Nov. 27, 1984 to Curtis A. Koontz for an INVALID TRANSFER DEVICE. This patent teaches a transfer device for carrying an individual and again, it utilizes a seat and harness assembly into which the patient cannot climb of his own volition but must be assisted into the chair and harness by outside human intervention. Once in place, the device is designed to transfer or move the patient from one location, to another but it is not designed in aiding the handicapped or disabled person in initially rising from a prone position on a bed to the sitting position.

Therefore, it can be readily seen that while the prior art recognizes the problem of building both the muscles and the self confidence of a prone patient by enabling him to lift himself to a sitting position with the weight of his upper body substantially over his hips without the assistance of another human being; and the present invention fills this long-felt need by providing such an apparatus while avoiding the various problems of the prior art.

The prior art does not teach any apparatus which aids a patient both psychologically and physically by enabling the patient himself, without outside human interference, to be able to raise himself or herself by using only a lift apparatus from a prone position to a sitting position. Furthermore, from this position, the patient can lock his muscles or the like and slide off of the bed into his wheelchair or other carrier in order to go to the bathroom, to his favorite chair, to eat, or to otherwise enjoy a more normal existence without requiring constant supervision and assistance from other humans.

While many of the lifts of the prior art are designed to lift a patient, most appear to be designed to lift a patient after he has been placed in some type of seat or bed-like arrangement and then move him from one place to another. The prior art does not seem to teach a device merely for enabling a patient to rise from a prone to a sitting position with the lift apparatus being stationery and not being used for any other purpose such as transporting the now-sitting patient from one location to another, from one bed to another, or the like.

BRIEF SUMMARY OF THE INVENTION

It is an object of the present invention to provide a portable motorized bed lift apparatus.

It is another object of the present invention to provide a portable motorized bed lift apparatus which can be used to enable a severely handicapped, disabled or injured patient to raise himself from a prone position on a bed to a sitting position with the weight of his upper body substantially over his hips without outside human intervention.

It is another object of the present invention to provide a bed lift apparatus for aiding severely handicapped or injured patients both physically, psychologically, and emotionally by enabling them to rise from a prone to a sitting position without requiring the assistance of another human being.

It is yet another object of the present invention to provide a portable motorized bed lift apparatus which can be remotely operated by a disabled or injured patient while lying prone on a bed or the like.

It is yet another object of this invention to provide a lift apparatus which can be either remotely actuated or actuated by switch means located on a handlebar to enable the apparatus to pull the patient upward and forward until he is in a sitting position with the weight of his upper body substantially over his hips.

It is yet another object of the present invention to provide a bed lift apparatus which, when activated by the patient, turns on a night light for a predetermined period of time to enable the patient to see what he is doing.

It is still another object of this invention to avoid substantially all the problems and difficulties of the prior art while solving the problem of enabling a prone patient to rise to a sitting position without outside human intervention.

The invention relates generally to a derrick-type apparatus having a motorized lift assembly comprising a conventional garage door opener apparatus. The derrick apparatus includes an upright mast which is secured in the upright position by support apparatus. The support apparatus includes a pair of elongated leg members which are preferably curved on the front and rear as runners or, alternatively, lockable castor wheels could also be used or anything equivalent thereto. A pair of angled support members and a base support serve to space the legs a predetermined distance apart and parallel to one another, while simultaneously supporting the upright mast. A boom member is pivotably mounted to the midportion of the mast. The outer end of the boom contains a plurality of spaced apart apertures for selectively adjusting the position of a distended handle or handle grip assembly so that it can be easily grabbed or grasped by the prone patient.

A cable has one end connected to the point of attachment of the handlebar and a midportion positioned over a pulley mounted atop the mast. The opposite end of the cable is attached to a trolley which is driven by another pulley arrangement up and down a guide rod by a set of motor-driven pulley cables. As the trolley is pulled down by the motor and pulley assembly, the cable raises the boom to approximately a 45° angle so that the upward component and horizontal component of the pull and the lift generates a circular arc at the point of attachment of the handlebar assembly so that the patient is both lifted vertically upward and pulled forward simultaneously for the optimum lift from a prone to a sitting position with the weight of his upper body substantially over his hips. Furthermore, a pair of generally trapezoidal plates are attached to the outer portion of the support assembly and each includes a front or forward facing slanted surface designed to abut against the rear edge of the bed for further bracing the derrick assembly against tipping and the like. For higher beds, a larger plate with a longer or higher float surface would be used.

Furthermore, the boom assembly may be telescopic, or otherwise adjustable in order to have its length shortened, or elongated as desired. Similarly, a push button or activator switch assembly is provided on a radio control apparatus, such as that conventionally used within a garage door opener to operate the motor assembly or, alternatively, a push button switch is located directly on the handlebar assembly so as to be engaged by the patient's hand, arm or the like. A light is illuminated when the switch is on to ensure that the patient can see what he is doing; and the light will remain on for $4\frac{1}{2}$ min. after each press of a switch, so as to illuminate the entire area in front of the lift apparatus. The elongated legs have at least the end portions thereof adapted to be positioned under the patient's bed from the bottom in so as to extend the boom upward until it is substantially over a position between the patient's groin area where his hands lay or his upper chest area, depending upon the ease with which he can reach the bar. The remote control device for motor actuation may be hand held or clipped to his bedding, pillow or the like, as known in the art.

These and other objects and advantages of the present invention will be more fully understood from reading the detailed description of the preferred embodiment, the claims, and the drawings which are briefly described hereinbelow.

DETAILED DESCRIPTION OF THE DRAWINGS

Figure 1:
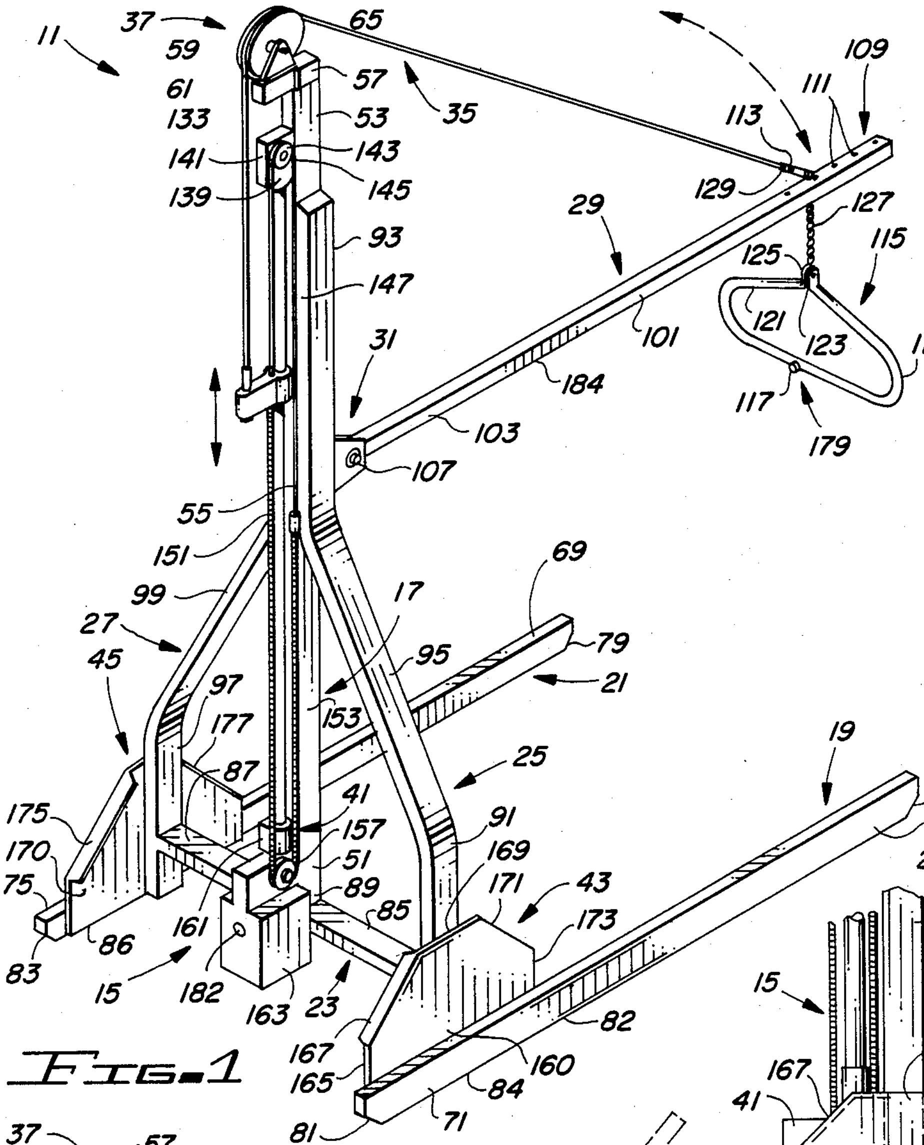
FIG. 1 shows a perspective view of the portable motorized bed lift apparatus of the present invention.

The portable motorized bed lift apparatus 11 of the present invention is shown in FIG. 1. The purpose of the lift is to enable a prone patient to achieve a sitting position with the weight of his upper body portion substantially positioned over his hips without requiring the outside assistance of another human being. Once in a sitting position, the patient can slide into a wheelchair, do one or more orthopedic exercises, or otherwise get out of bed for any number of purposes.

The lift apparatus 11 includes a derrick-like assembly 13 and a power train assembly 15. The derrick assembly 13 includes a generally vertically upright mast 17; a pair of elongated leg or feet members 19, 21; a lateral or base support 23; a pair of angled upright supports 25, 27; and a boom member 29.

The vertically upright mast 17 includes a first or lower end portion 51, a second or upper end portion 53, and a central or intermediate portion 55. The first or right elongated foot or leg member 19 includes a first or forward end portion 67 and a second or rearward portion 71. The distal front end of the forward end portion 67 is generally slanted or curved to present a curved outwardly from the bottom to the top to present a curved surface 77 while the distal end of the rear portion 71 is also tapered or curved from the bottom to the top to present a curved surface 81 so that the elongated member 19 functions as a sled-type runner. Similarly, the second or left elongated leg 21 includes a first or forward end portion 69 and a second or rear end portion 75. The front end portion similarly terminates in a curve or taper 79 while the rear distal end portion terminates in a taper or curve 83 to provide a second sled-type runner.

The elongated runner-type leg members 19 and 21 each have a longitudinal axis and a longitudinal axis of the members 19 and 21 are substantially parallel to one another and perpendicular to the longitudinal axis of the lateral support or base support member 23. The base support member 23 has a first or right hand end portion 85 and a second or left hand portion 87. The lower distal end 89 of the mast 17 is operatively disposed on and secured to a midportion of the base support member 23.

The righthand angled member 25 of the support 13 includes a relatively straight vertically disposed lower end portion 91, a relatively straight vertically disposed upper end portion 93, and a relatively straight diagonal midportion 95 which integrally connects vertically disposed end portions 91 and 93. The vertical axis of the lower end portion 91 is generally parallel to and spaced apart from the vertical axis of the upper end portion 93 and the intermediate diagonal portion 95 interconnects the two end portions to form a single unitary integral brace 95. The lefthand angled brace member 27 has a relatively straight vertical lower end portion 97, a relatively straight vertical upper end portion, not shown, but similar to upper end portion 93 of brace 25, and an intermediate diagonal interconnecting portion 99. Similarly, the axis of the lower end portion 97 and the upper end portion, not shown, are parallel to and spaced apart from one another and the intermediate interconnecting portion 99 interconnects the upper and lower end portions to form a single integral unitary angled brace 27.

The lower end portions 91 and 97 are operably disposed proximate the distal end portions 85 and 87, respectively, of the base member, cross support or lateral support 23 and secured thereto. The outer end portions are attached through sloping means 43,45 having a righthand trapezoidal plate member 160 and a lefthand trapezoidal plate member 170 to the inside surface of the rear end portions 71 and 75 of the elongated leg members 19 and 21, respectively. The axis of the cross support or base support 23 is generally perpendicular to the longitudinal axis of the leg members 19 and 21 and is also perpendicular to the longitudinal vertical axis of the lower end portions 91 and 97 of the angled supports 25 and 27, respectively; and is further perpendicular to the longitudinal axis of the mast 17. The plate members 160 and 170 are generally trapezoidal in form. Plate 160 includes a relatively straight lower edge 84 adapted to be disposed on the floor; a pair of vertically upright sides 165 and 173 extending therefrom; and a relatively straight upper end portion 169 generally parallel to and shorter than the bottom edge 84 and 86, respectively. The righthand plate 160 has a slanted leading or front edge 171 interconnecting the vertical forward edge 173 and the relatively shorter top edge 169 at an acute angle and a the similar slanted surface 167 interconnects the top edge portion 169 with the vertical edge 165 at the rear of the support apparatus 13. The function of the slanted surface 171 will be described hereinafter with reference to FIG. 3. Similarly, the plate 170 has a forward slanted surface 177, a corresponding rear slanted surface 175 a lower edge 86, upper edge 172, a front edge 174, and a rear edge 164 as shown in FIG. 1.

The boom assembly 29 includes a generally rectangular elongated boom member 101 having a forward end portion 109 and a rearward end portion 103. The rearward end portion 103 is pivotably attached to a mid portion of the mast 17 by pivotable mounting assembly 31. The assembly 31 includes a pair of spaced apart ear-like members 105 with an open channel therebetween for receiving the rear end portion 103 of the boom member 101 therein and a pivot pin 107 passes through the ear-like members 105 and the end portion 103 for securing the boom 29 to the midportion of the mast 17 for pivotable movement about the axis of the pivot pin 107. The outer or forward end portion 109 of the boom 101 includes a plurality of spaced apart drilled holes or apertures 111 to which a fastening member 113 may be manually positioned to determine the particular desired location of the handle assembly 33 with respect to the distal end of the forward end portion 109 and with respect to the positioning of the handle apparatus 33 above the patient.

The handle apparatus 33 includes an elongated relatively straight bar portion 117, a pair of curved upright portions 119, and a pair of slanted portions 115 connecting the upright portions 119 to a pair of ear-like members 123. A distended chain-type apparatus 127 can be positioned between the ear-like members 123 and secured therein by a bolt or similar fastening means 125 so as to operatively connect the suspended handle portion 33 to the chain 127 whose upper end is connected via connector 113 to the end 109 of the boom 101. In the preferred embodiment of the present invention, the lower portion 117 of the handle apparatus 33 is provided with a switch means 179 which can be used to activate the motorized apparatus of the present invention when contacted by the patients hand, wrist, forearm, inner elbow, upper arm, armpit, or the like.

A cable 35 has one end portion 129 operatively secured to the adjustably positionably connector 113 of the handle apparatus 33 and further includes a midportion 133 and a lower end portion 131. A pulley assembly 37 is operatively mounted atop the mast 17 on a pulley mounting portion 57. The pulley assembly 37 includes a conventional pulley 59 having a peripheral groove 61 extending completely about the periphery thereof for receiving the intermediate portion 133 of the cable-like member 35. The pulley 59 has a pivot pin 65 extending through a central aperture therein and a pair of ear-like members 63 operatively positioned to secure the ends of pivot pin against motion while permitting the pulley 59 to rotate about the pin 65 as known in the art. The opposite end portion 131 of the cable-like member 35 is connected to the trolley apparatus 39.

The trolley apparatus 39 reciprocates vertically up and down on a rigid guide rod 137 which has one end operatively secured within a brace means 139 at a pulley support 141 and its opposite end operatively fixedly secured within a lower collar member 161 proximate the motor 163. One end portion of the cable-like member 149 is operatively secured to the upper portion of the trolley 39 while the remaining portion of the cable-like portion 139 passes over the groove of the pulley of the trolley idler pulley 143 which rotates on pin 145 and the remaining portion 147 extends to an interconnector 155 which connects the upper cable-like member to a lower sprocket chain link or chain-like member 153 which in turn is wrapped about a drive pulley or drive sprocket 157 mounted on drive pin 158 as the opposite end passing about the pulley 157 continues until its end portion 151 is secured to the bottom or lower end of the trolley 39.

A motor 163 which can be remotely controlled by a conventional remote control unit, not shown, but conventionally known in the art or by a switch 179 or 180 on the handle portion 33 is positioned at the lower end of the support assembly 13 proximate the upright mast 17. The motor drives the sprocket gear 157 which in turn rotates either clockwise or counterclockwise to turn the chain or pulley cord-like member 153 which in turn raises or lowers the trolley 39. Alternately, a gear-driven drive, worm gear or the like could also be used in place of the pulley arrangement. As the trolley is pulled downward, the lower distal end 131 of the cord-like member 35 is pulled downward over the groove 61 of the pulley 59 causing the outer end of the boom 101 to be pulled upward and rearward since the cable makes an acute angle with the boom of both the vertical component of lift and a horizontal component of pull applied to the handle to lift and pull the patient up from the prone position to a sitting position wherein the weight of the patient's upper body portion is substantially over his hips thereby enabling him to lock his muscles or joints and position himself for exercises, for motion into a wheelchair, or the like.

It will also be noted that the switches 179 and 180, and the remote control unit, not shown, are used to activate the motor drive and may also be used to turn on the light 182. This will provide sufficient illumination forward of the mast 17 to enable the patient to clearly see the handle apparatus 33 prior to completely being raised to the sitting position and to enable him to see his wheelchair or whatever he must see in order to get out of bed or to do his exercises or the like. A light, night-light or similar illumination means is conventionally carried on the motor 163 but could also be carried on the mast 17 and turned on by the remote control unit and/or the switch 179, 180.

Figure 2:
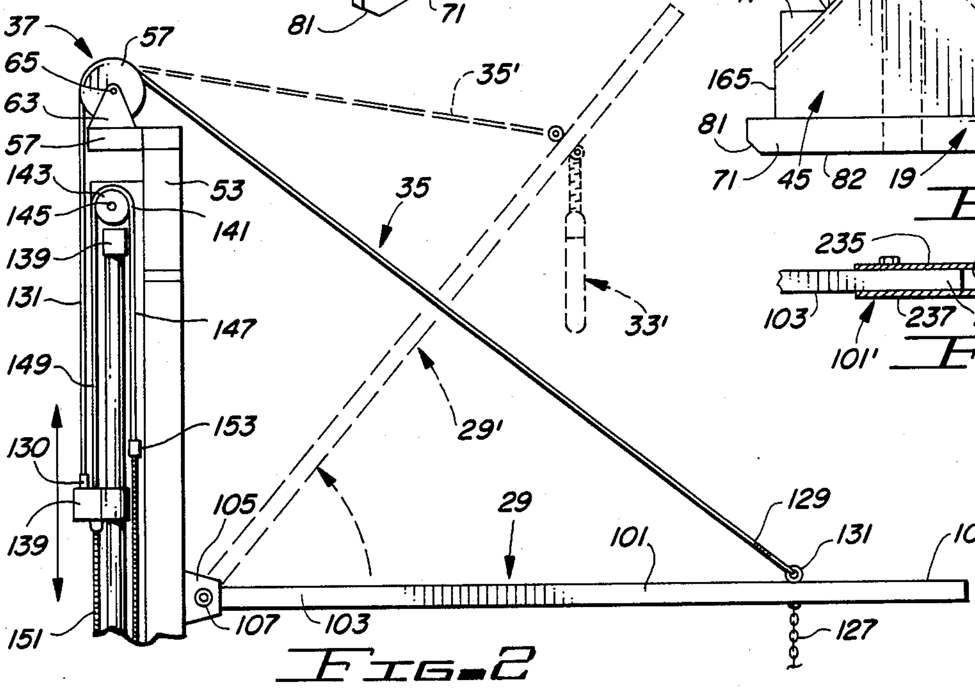
FIG. 2 shows a partially cut away side view of the boom and upper end portion of the mast assembly of the apparatus of FIG. 1 in both a fully extended horizontal position and an activated raised position.

FIG. 2 shows the upper end portion 53 of the vertical mast 17 and the boom apparatus 29 both in the inactive or down position and in the activated or up position. In FIG. 2, it can be seen that the boom 29 has the elongated member 101 positioned in the down position wherein the axis of the member 101 is substantially parallel to the ground and perpendicular to the longitudinal axis of the upright mast 17. However, after the mast 101 has been raised to the acute angle shown in phantom lines, it may be observed that the handle 33' has been raised to a position such that the patient grasping the handle has been both lifted vertically upward and moved horizontally to the left so as to enable the patient to achieve a sitting position, without the outside assistance of any human being, so that he is then sitting in a position with the weight of his upper body substantially over his hips so as to enable him to tighten his muscles or the like to maintain this position or even to slide out of bed into a wheelchair or the like. It will be seen that the angle required for the optimal lift approaches 45°.

Figure 3:
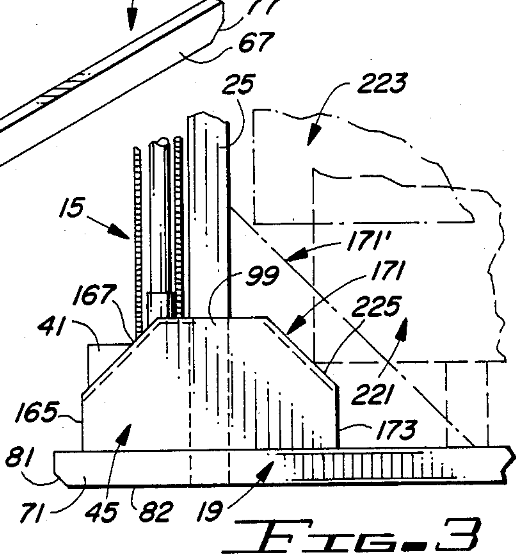
FIG. 3 illustrates the support assembly of the lift apparatus of FIG. 1 engaging different height beds.

FIG. 3 shows the function of the leading slanted edge 171 of the base support plate 160, as being operable to engage the lower edge portion of a conventional bed 221 when the elongated legs 19 and 21 are operatively disposed at least partially under the bed until the lower edge of the bed contacts the surface 171 at point or edge 225. This adds still additional stability to the lifting apparatus 11 of the present invention and assists further in preventing tipping and aiding in absorbing the torque of the lift. It will also be seen by the phantom line 171', that the vertical surface 171 can be extended outward and upward for engaging the lower edge of a higher bed, such as a hospital bed or the like, as at a point 227 to provide similar added stability and the like.

Figure 4:
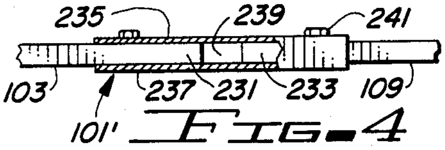
FIG. 4 illustrates a partial view of an alternate embodiment of the boom assembly of FIG. 1 which can have its length selectively adjusted.

FIG. 4 shows that the boom apparatus 29 may include an elongated boom member 101 which is segmented, telescopic, or otherwise extendible or reducible for varying the length thereof depending on the distance from the bottom of the bed to the point at which the patient can grasp the handle when the degree of adjustability of the apertures or screw holes 111 is insufficient. In FIG. 4, a first end 231 of end portion 103 of the boom 101 is shown as being inserted into the hollow channel formed by sides 235 and 237 while the opposite 233 of end portion 109 of the boom 101 is inserted into the opposite end of the channel formed by members 235 and 237. The members may be positioned a distance apart so that a hollow channel portion still exists between their distal ends, as indicated by reference numeral 239 and their end portions 231 and 233 can be secured at that position as by nut and bolt assemblies 241 passing through the members 235 and 237 so as to adjustably position the boom at a given length. Various means are known in the art for telescoping or positioning such elements for increasing or decreasing the extended length of a member of any of these means can be used with the present invention.

Figure 5:
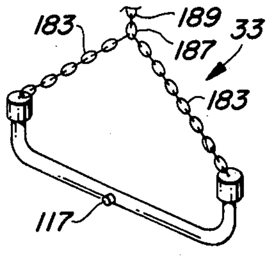
FIG. 5 is a perspective view of an alternate embodiment of the handle assembly of the lift apparatus of FIG. 1.

FIG. 5 illustrates an alternate embodiment of the handle assembly 33 of FIG. 1 and shows the generally horizontal lower bar 117 as having a pair of vertically upwardly extending portions 181 topped by cap members 185. Each of the cap members are connected by chains or cord-like means 183 to a common chain link 187 which is then connected to a vertically distending chain 189, which could be the end link 127 of FIG. 1. Similarly, the lower bar 117 of the handle assembly 33 of FIG. 5 is provided with a switch mechanism 180 which could be activated by the patient to operate the motorized assembly of the present invention.

Figure 6:
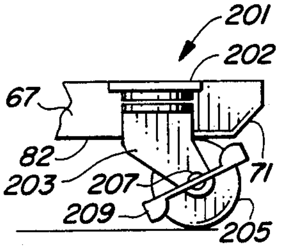
FIG. 6 is an alternate embodiment of the elongated runner elements of FIG. 1 provided with lockable caster wheels.

FIG. 6 shows the forward end portion 67 of the elongated member 19 in which the lower edge 82 is not disposed on the floor in a sled-like runner fashion but which, instead, is provided with a wheel assembly 201. The wheel assembly 201 includes a caster socket base 202 to which is mounted a rotatable leg portion 203, and a wheel 205 is operatively mounted to the plate 203 by an axel 207. A locking means 209, which can be manually turned to lock or secure the position of the wheel 205 at any given point thereby preventing the members 19, 21 from rolling out from under the bed or about under the bed once the locking means 209 has been engaged.

With reference to FIG. 1, it will be noted that the portable motorized bed lift apparatus 11 is designed to lift a prone patient to a sitting position on the bed without the assistance of another human being so that the patient can get into a wheelchair, be positioned upright for doing certain required therapeutic exercises, or to be positioned for getting out of bed for any number of reasons. The motorized unit can be easily adjusted to any desired beginning and end position in and incremental amounts, or distances can be established by switch actuations. It may utilize, a conventional remote control device such as that used with conventional garage door openers wherein a button on a hand-held unit can be manually-activated to raise and lower the unit or it can be operated by directly-wired controls from switch means located on the handle bar assemblies themselves. The lift apparatus of the present bed preferably includes legs or runners or sled-like runners that are adapted to go under the bed from the bottom foot end toward the top or head end in order to take the torque of the pull and lift while the angle supports of the forward edge of the plates on the supports are adapted to lock under the lower edge of the bed for still additional leverage and the like. It will be understood that the elongated legs can be placed under the bed in other than a direction generally parallel to the longitudinal axis of the bed. They can, for example, be positioned more to one side or the other such that as the patient is lifted and pulled to a sitting position, he or she is in the proper location and positioned with the proper alignment for exiting the bed or the like.

It will also be understood that the motorized drive train portion 15 of the lift apparatus 11 is actually a conventional garage door opener such as that manufactured by the Clopay Corp. as model no. DPD 167-83, 1983. The garage door opener is mounted upright and vertically instead of horizontally and is used to lift rather than pull, but it is more than adequate for use in the present invention.

Furthermore, the engagement of the slanted, forward-facing surfaces 171 and 177 of the support plate members 43 and 45, respectively, also serve to prevent "creep" of the apparatus during the lifting operation; and the normal friction of the surface of the floor against the runner type members 19 and 21 serves to prevent sliding, particularly since the torque is experienced more at the forward end of the legs positioned substantially under the bed.

Several other unique features of the present invention will now be discussed. A hand grip bar is located on or near the booms end, and a series of evenly-spaced holes or drilled apertures on the boom permit locating the hand grip precisely for the individual patients convenience and requirements. Since some prone patients will not be able to reach up with their arms and grasp the hand grip with their hands, it may be necessary to adjust the hand grip bar further to the rear on the boom and to lower it to the patient's extended arm length at or near the pelvic region. Furthermore, if the patient's hands and wrists are too weak to grasp and hold the handle bar for lifting, other types of grips may be employed and the bar may be grasped with the forearm or inner elbow, with the arm pit, or the like.

In the preferred embodiment, the lift hand grip or handle bar assembly is raised and lowered to within the patients reach by means of a remote controlled radio transmitter. This remote control unit can be clipped to the patient's bed wear or the bed and the direction of vertical travel can be changed with each press of the button. The control can be pre-set at appropriate up-stop and down-stop positions depending upon each patient's need. The boom will come to an intermediate stop with a press of a button. The safety system of the present system also provides for instant reversing, as required. Furthermore, the lift and forward pull action which is necessary for properly lifting the patient is initiated when the boom end and handle bar are raised. The movement is activated by the prone patient grasping the bar and pressing a second transmitter control button located on the bar in the preferred embodiment. The action stops automatically when the patient has attained the predetermined upright sitting position.

An additional feature of the bed lift of the present invention is the inclusion of an automatic night light or illumination means. If the patient must use the lift apparatus during the night, the light comes on and remains lit for a predetermined period of time, such as $4\frac{1}{2}$ minutes, after each press of the transmitter button. In this manner, the patient can provide himself with a period of illumination depending upon the need for which he saw fit to raise himself to the sitting position.

The portable motorized lift apparatus of the present invention represents a significant step forward in providing greater patient mobility and independence. It totally eliminates the need for any second person's assistance. There is no harness of any kind required and the patient does not require either assistance or unusual abilities to climb into a harness for lifting or transporting purposes. Furthermore, no batteries are required. The bed lift further offers a wide variety of benefits and convenience for bedridden or bed prone patients. Equally important to its potential use in the home care of patients and the like, lies in fields of physical therapy and rehabilitation where the lift apparatus can be used to enable the patient to perform or position himself to perform many required exercises and the like.

Since the apparatus of the present invention is normally positioned under the lower end of the bed facing toward the head, it never takes up more floor space than 12 inches by 24 inches at the foot of the bed thereby leaving the sides of the bed clear for transport equipment like wheelchairs, scooters, stretchers, and the like. It may never have to be moved once it is placed under the bed but since it is not attached to anything, it can be pushed away on its sled-type runners or the like to another bed for use by someone else or for cleaning purposes and the like.

The motor of the garage door assembly operates on any 110 AC outlet and can be controlled by a conventional hand-held control unit or a radio transmitter clipped on the patient's clothing or the like. It can also be controlled either independently or in cooperation with switching means located on the handle itself.

The power train mechanism, as previously explained, is a garage door opener wherein the power train is used without changes of any type except for reducing the length of the track tube or guide tube and the lengths of the chain cable to compensate for this reduction. The garage door opener used in the preferred embodiment of the present invention has many advantages including the fact that it is factory pre-tested, and installs in minutes, is sold pre-assembled or in a knock down version, has an external safety and limit switch adjustments, meets or exceeds all published safety requirements, has a five year warranty, has a one third horse power motor made to handle 16 foot doors with ease, can be advanced in digital increments with electronic controls and is made to provide a $4\frac{1}{2}$ minute light delay, is easy to set or program with individual codes, has wide dealer support, and the like.

In the preferred embodiment, the support braces are very strong and are normally made from rectangular or square steel tubing. The horizontal legs supports have sled-type runners on the front and rear for easy moving, and the legs are slid under the foot of the bed with the boom and the handle dropping wherever its best for the patient. A stirrup-type handle is normally used on the handlebar apparatus and a control button is appropriately placed at the side or in the center of the handlebar, as required. The boom is pivoted or hinged to the upright mast at approximately the 34 inch line or near the midpoint of the upright mast. This height with the pulley mounted on top of the mast provides a natural angle of pull which automatically raises the prone patient to the desired sitting position.

The stopping edge at the bottom of the support assembly is made to engage the bottom edge of the box springs or frame of the bed and increased the stability of the derrick assembly. This also anchors the bed and the derrick and allows room for making the bed. Furthermore, it increases the torque-absorbing capacity of the system and further prevents tipping and the like.

With this detailed description of the specific apparatus and structure used to illustrate the preferred embodiment of the present invention and the operation thereof, it will be obvious to those skilled in the art that various modifications, changes and variations can be made in the design, construction and materials and in the method contemplated thereby without departing from the spirit and scope of the present invention which is limited only by the appended claims.

I claim:

1. A portable motorized bed lift apparatus for lifting a prone patient to a sitting position on a bed such that the patient's head and shoulders are substantially vertically above the patient's hips to enable the patient to get out of bed and into a wheelchair or the like without human assistance, said lift apparatus comprising:

leg means including a spaced apart pair of elongated leg members having a front portion and a rear portion, said leg members adapted to be operably disposed substantially parallel to one another and such that said front portion is operatively disposed at least partially under the foot of the patient's bed for countering the torque of the lifting action to prevent tipping and the like;

base means operatively disposed between the rear end portions of said pair of leg members and being disposed substantially perpendicular thereto for maintaining said spaced separation;

mast means including an elongated, vertically upright mast member having a lower end portion operatively secured proximate the midportion of said base means and being substantially perpendicular to the longitudinal axis of said base means and to the longitudinal axis of said leg members, said mast member further including a mid-portion and an upper end portion;

support means including a pair of generally upright angled members each having a relatively straight lower end portion adapted to be operatively secured in a vertically upright position to opposite end portions of said base means and to said rear end portion of said leg members so as to be substantially perpendicular to the longitudinal axis thereof, an upper end portion operatively secured in a vertically upright position to opposite sides of the midportion of said vertically upright mast member so as to be substantially parallel thereto, said upper and lower end portions of each of said angled members having longitudinal axes which are parallel to and spaced apart from one another, each of said pair of angled members including an intermediate diagonal portion integral with said vertically upright upper and lower end portions for forming a single unitary, integral, angled support member;

an elongated boom member pivotably attached to a pivot means at a rear end portion thereof and to said midportion of said upright mast member such that the forward end portion of said boom is free to swing in a circular arc about said pivot means;

handle means operatively suspended from a selected position on said forward end portion of said boom means for enabling the patient to grasp said handle means with at least one of his hands, wrists, inner elbow, and arm pits;

pulley means operatively disposed atop said mast member;

cable means having an intermediate portion operably positioned over said pulley means, one end portion operatively coupled to a forward end of said boom means proximate the attachment point of said handle means, and an opposite end portion;

trolley means including a vertical guide post operably disposed generally parallel to said mast member, means associated with said trolley means for operatively connecting the opposite end portion of said cable means thereto for raising and lowering said boom and said handle means as said trolley means is vertically lowered and raised on said guide post;

motor drive means including a motor, a drive sprocket means rotatably driven by said motor, an upper idler pulley means operatively mounted to an upper end portion of said mast member, said drive means for running a chain-like drive assembly, said motor drive means having a drive mechanism and a chain-like member passing around the sprocket means of said drive assembly being rotatably driven thereby, one end portion of said chain-like member being operatively coupled to a bottom portion of said trolley means and the opposite end of said cable-like member being connected to one end of a cable having an intermediate portion passing over said upper pulley and downward so that the opposite end portion is secured to the top of the trolley such that when the motor is operated in the forward or reverse direction, the trolley is moved selectively down and up to selectively position the boom up and down in a circular arc so as to provide a vertical lift component and a horizontal pull component to enable the patient to be lifted to the proper sitting position.

2. The lift apparatus of claim 1 wherein each of said pair of elongated leg members includes a runner-like portion having a relatively flat bottom and upwardly curved end portions for enabling the lift apparatus to be slidably positioned under at least a portion of the patients bed from the foot end.

3. The lift apparatus of claim 1 further including illumination means operatively mounted to the motor near the radio receiver for illuminating the patient's bed and the handle means suspended from the boom member, said illumination means being manually operable by said patient.

4. The lift apparatus of claim 1 wherein said motor drive means includes a radio receiver operatively coupled to said motor for selectively driving same and a remote radio transmitter adapted to be operated by said patient for controlling the operation of said motor through signals transmitted and received by said receiver means.

5. The lift apparatus of claim 1 wherein said handle means further includes switching means activated by contact with at least a portion of the patients hand, wrist, lower arm, inner elbow, upper arm, and arm pit for electrically operating said motor drive means in response to the operation of said switching means by said patient.

6. The lift apparatus of claim 1 wherein said support means includes a pair of forwardly facing surface means for operatively engaging the bottom end portion of a bed of a given height to prevent creep and further increase the stability of the apparatus.

7. A portable lift apparatus for lifting a prone patient to a sitting position on the patient's bed without the assistance of another human being so as to enable the patient to get out of bed, to do exercises, and the like, said lift apparatus comprising:

an elongated, relatively straight mast having a lower end portion, an upper end portion, and an intermediate portion;

support means for maintaining said mast in a fixed vertical position, said support means including a pair of elongated leg means adapted to be positioned at least partially under the patient's bed from the foot end for taking the torque generated during the lifting operation;

a boom means having one end pivotably secured to said intermediate portion of said mast such that the opposite end is free to swing in a circular arc whose radius is equal to the effective length of the boom;

handle means operatively suspended from a desired location on the opposite end of said boom means for enabling the prone patient to engage the handle means for lifting said patient to a sitting position;

pulley means operatively disposed atop said mast;

an elongated flexible connector means having an intermediate portion operatively disposed over said pulley means, having one end portion operatively secured to a selected position on the opposite end portion of said boom means, and having an opposite end portion;

trolley means including a vertical guide for enabling said trolley means to reciprocate vertically up and down, said trolley means including means for operatively securing said opposite end portion of said connector means thereto for raising and lowering said boom as said trolley means is raised and lowered;

sprocket and pulley means for selectively raising and lowering said trolley means;

motor means for driving said sprocket and pulley means; and motor control means operably disposed within easy reach of said prone patient for enabling said prone patient to selectively operate said motor means.

8. The portable lift apparatus of claim 7 wherein said elongated leg means include a pair of elongated runner-like members adapted to be slidably positioned under the patient's bed.

9. A portable lift apparatus for lifting a prone patient to a sitting position on the patient's bed without the assistance of another human being so as to enable the patient to get out of bed, to do exercises, and the like, said lift apparatus comprising:

an elongated, relatively straight mast having a lower end portion, an upper end portion, and an intermediate portion;

support means for maintaining said mast in a fixed vertical position, said support means including a pair of elongated leg means adapted to be positioned at least partially under the patient's bed from the foot end for taking the torque generated during the lifting operation;

a boom means having one end pivotably secured to said intermediate portion of said mast such that the opposite end is free to swing in a circular arc whose radius is equal to the effective length of the boom;

handle means opertively suspended from a desired location on the opposite end of said boom means for enabling the prone patient to engage the handle means for lifting said patient to a sitting position;

pulley means operatively disposed atop said mast;

an elongated flexible connector means having an intermediate portion operatively disposed over said pulley means, having one end portion operatively secured to a selected position on the opposite end portion of said boom means, and having an opposite end portion;

trolley means including a vertical guide for enabling said trolley means to reciprocate vertically up and down, said trolley means including means for operatively securing said opposite end portion of said connector means thereto for raising and lower said boom as said trolley means is raised and lowered;

sprocket and pulley means for selectively raising and lowering said trolley means;

motor means for driving said sprocket and pulley means; and motor control means including a radio receiver means for receiving signals indicative of the desired operation of said motor for controlling same and a remote transmitter unit adapted to be operated by the prone patient for sending control signals to said receiver means.

10. A portable lift apparatus for lifting a prone patient to a sitting position on the patient's bed without the assistance of another human being so as to enable the patient to get out of bed, to do exercises, and the like, said lift apparatus comprising:

an elongated, relatively straight mast having a lower end portion, an upper end portion, and an intermediate portion;

support means for maintaining said mast in a fixed vertical position, said support means including a pair of elongated leg means adapted to be positioned at least partially under the patient's bed from the foot end for taking the torque generated during the lifting operation;

a boom means having one end pivotably secured to said intermediate portion of said mast such that the opposite end is free to swing in a circular arc whose radius is equal to the effective length of the boom;

handle means operatively suspended from a desired location on the opposite end of said boom means for enabling the prone patient to engage the handle means for lifting said patient to a sitting position;

pulley means operatively disposed atop said mast;

an elongated flexible connector means having an intermediate portion operatively disposed over said pulley means, having one end portion operatively secured to a selected position on the opposite end portion of said boom means, and having an opposite end portion;

trolley means including a vertical guide for enabling said trolley means to reciprocate vertically up and down, said trolley means including means for operatively securing said opposite end portion of said connector means thereto for raising and lowering said boom as said trolley means is raised and lowered;

sprocket and pulley means for selectively raising and lowering said trolley means;

motor means for driving said sprocket and pulley means; and motor control means including switching means operatively carried by said handling means for enabling said prone patient to control the operations of the motor means once said patient has engaged said handle means.

11. The portable lift apparatus of claim 10 further including illumination means operatively mounted to said mast for illuminating the patient, bed, and handle means, said illumination means being turned on for a predetermined fixed period by said patient.

12. The portable lift apparatus of claim 10 wherein said support means further include forwardly disposed slanted surface means for engaging the lower edge portion of the patients bed for preventing "creep" and further increasing the stability of the apparatus.

13. A portable motorized lift apparatus for assisting a prone patient on a bed who cannot sit up under his own power due to the fact that the patient is crippled, injured, or otherwise incapacitated to achieve a sitting position on the bed without the assistance of another human being and such that the weight of the patient's upper body and head is substantially positioned over his hips thereby enabling the patient to do therapeutic exercises or the like from the sitting position or to tense his muscles or joints so as to be able to control his body and slide off of the bed and into a wheelchair of the like for various purposes, said lift apparatus comprising:

gripping means adapted to be grasped by at least one of the patients hands, wrists, forearm, inner elbow, upper arm, and arm pit;

derrick means including a boom means for suspending said gripping means in a desired position above the prone patient so as to enable the patient to grasp the gripping means as required;

said derrick means further including an upright beam and means for supporting same in a vertically upright position;

pulley means operatively mounted atop said upright beam;

trolley means including a trolley, a vertical upright support guide post, and an idler pulley operatively coupled to an upper portion of said upright beam;

cable means operatively disposed over said pulley means and having one end operatively coupled to the front end portion of said boom and the opposite end portion operatively coupled to said trolley for enabling said boom to be raised and lowered as said trolley is lowered and raised;

motor drive means including a motor, motor control, and a sprocket drive, and drive means operatively coupled about said sprocket drive and over said idler pulley such that one end is operatively coupled to the top of said trolley and the opposite end is coupled to the bottom of said trolley for raising and lowering said trolley by operating said motor in forward or reverse directions; and manually operable means for enabling the prone patient to selectively control the operation of said motor and hence the raising and lowering of said gripping means, as desired and without the assistance of a second party.

14. The lift apparatus of claim 13 wherein said derrick means further includes a pair of elongated leg members adapted to be positioned substantially under the patient's bed from the foot thereof.

15. The lift apparatus of claim 14 wherein said elongated members are sled-type runners having a relatively flat lower portion for frictionally engaging the floor and upwardly curved end portions to facilitate sliding in a desired direction.

16. The lift apparatus of claim 14 wherein said elongated leg members include lockable wheels for enabling said support means to quickly and easily be positioned to patient's bed and the wheels locked at a desired location to prevent further movement thereof.

17. A portable motorized lift apparatus for assisting a prone patient on a bed who cannot sit up under his own power due to the fact that the patient is crippled, injured, or otherwise incapacitated to achieve a sitting position on the bed without the assistance of another human being and such that the weight of the patient's upper body and head is substantially positioned over his hips thereby enabling the patient to do therapeutic exercises or the like from the sitting position or to tense his muscles or joints so as to be able to control his body and slide off of the bed and into a wheelchair of the like for various purposes, said lift apparatus comprising:

gripping means adapted to be grasped by at least one of the patients hands, wrists, forearm, inner elbow, upper arm, and arm pit;

derrick means including a boom means for suspending said gripping means is a desired position above the prone patient so as to enable the patient to grasp the gripping means as required;

said derrick means further including an upright beam and means for supporting same in a vertically upright position;

pulley means operatively mounted atop said upright beam;

trolley means including a trolley, a vertical upright support guide post, and an idler pulley operatively coupled to an upper portion of said upright beam;

cable means operatively disposed over said pulley means and having one end operatively coupled to the front end portion of said boom and the opposite end portion operatively coupled to said trolley for enabling said boom to be raised and lowered as said trolley is lowered and raised;

motor drive means incuding a motor, motor control, and a sprocket drive, and drive means operatively coupled about said sprocket drive and over said idler pulley such that one end is operatively coupled to the top of said trolley and the opposite end is coupled to the bottom of said trolley for raising and lowering said trolley by operating said motor in forward or reverse directions; and manually operable motor control means manually operable including a remote control radio transmission device adapted to be at least one of hand-held and attached proximate the patient for enabling the prone patient to utilize the remote control radio transmission device for controlling the operation of said motor and hence the raising and lowering of said gripping means.

18. A portable motorized lift apparatus for assisting a prone patient on a bed who cannot sit up under his own power due to the fact that the patient is crippled, injured, or otherwise incapacitated to achieve a sitting position on the bed without the assistance of another human being such that the weight of the patient's upper body and head is substantially positioned over his hips thereby enabling the patient to do therapeutic exercises or the like from the sitting position or to tense his muscles or joints so as to be able to control his body and slide off of the bed and into a wheelchair of the like for various purposes, said lift apparatus comprising:

gripping means adapted to be grasped by at least one of the patients hands, wrists, forearm, inner elbow, upper arm, and arm pit;

derrick mean including a boom means for suspending said gripping means in a desired position above the prone patient so as to enable the patient to grasp the gripping means as required;

said derrick means further including an upright beam and means for supporting same in a vertically upright position;

pulley means operatively mounted atop said upright beam;

trolley means including a trolley, a vertical upright support guide post, and an idler pulley operatively coupled to an upper portion of said upright beam;

cable means operatively disposed over said pulley means and having one end operatively coupled to the front end portion of said boom and the opposite end portion operatively coupled to said trolley for enabling said boom to be raised and lowered as said trolley is lowered and raised;

motor drive means including a motor, motor control, and a sprocket drive, and drive means operatively coupled about said sprocket drive and over said idler pulley such that one end is operatively coupled to the top of said trolley and the opposite end is coupled to the bottom of said trolley for raising and lowering said trolley by operating said motor in forward or reverse directions; and motor control means including a manually-operable switch operably disposed on said gripping means for enabling the prone patient to manually control the operation of said motor means and hence the raising and lowering of said gripping means.

19. The lift apparatus of claim 13 further including illumination means operatively mounted on at least one of an upper end portion of said upright beam beneath said pulley means and above said mid portion and on said motor drive means, said illumination means being responsive to the operation of said motor control means for turning on to provide a predetermined period of illumination for the patient while attempting to grasp said gripping means and to raise himself to the required sitting position.

20. The lift apparatus of claim 13 wherein said derrick means further include a pair of forwardly facing slanted surface means for operatively engaging the lower bottom edge of the patients bed for preventing creeping, for further preventing tipping, and for further stabilizing said derrick means.

* * * * *

UNITED STATES PATENT AND TRADEMARK OFFICE

CERTIFICATE OF CORRECTION

PATENT NO. : 4,644,595

DATED : February 24, 1987

INVENTOR(S) : R. A. Daniel

It is certified that error appears in the above-identified patent and that said Letters Patent is hereby corrected as shown below:

Title page:

Item [45] Date of Patent: "Feb. 24, 1984" should read -- Feb. 24, 1987 --.

Signed and Sealed this

Sixteenth Day of August, 1988

*Attest:*

DONALD J. QUIGG

*Attesting Officer*

*Commissioner of Patents and Trademarks*